United States Patent [19]

Kehrli, Jr. et al.

[11] Patent Number: 5,234,810
[45] Date of Patent: Aug. 10, 1993

[54] DIAGNOSTIC ASSAYS FOR GENETIC MUTATIONS ASSOCIATED WITH BOVINE LEUKOCYTE ADHESION DEFICIENCY

[75] Inventors: Marcus E. Kehrli, Jr., Colo; Dale E. Shuster, Ames, both of Iowa

[73] Assignee: The United States of America as represented by the Secretary of Agriculture, Washington, D.C.

[21] Appl. No.: 764,466

[22] Filed: Sep. 20, 1991

[51] Int. Cl.$^5$ .............. L12Q 1/68; C07H 21/04; C12N 15/00; C12P 19/34
[52] U.S. Cl. ....................... 435/6; 536/23.5; 935/77; 935/78; 435/91
[58] Field of Search .............. 435/6, 91; 536/27, 23.5; 935/77, 78

[56] References Cited

PUBLICATIONS

Law et al, Embo J, vol. 6, 1987, pp. 915–919.
Kishimoto et al, Cell, vol. 48, Feb. 27, 1987, 681–90.

*Primary Examiner*—Margaret Moskowitz
*Assistant Examiner*—Mindy B. Fleisher
*Attorney, Agent, or Firm*—M. Howard Silverstein; John D. Fado; Curtis P. Ribando

[57] ABSTRACT

A point mutation in the CD18 gene responsible for causing bovine leukocyte adhesion deficiency (BLAD) and a silent mutation linked thereto have been identified. Nucleic acid sequences encompassing these mutations serve as bases for testing and identifying cattle alleles attributable to BLAD using any of a variety of diagnostic assays. Suitable nucleic acid probes and primers have also been designed for use in such assays.

14 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Bos taurus ( i x ) FEATURE:
    ( A ) NAME/KEY: mutation
    ( B ) LOCATION: replace(41, "g")

( x i ) SEQUENCE DESCRIPTION: SEQ ID NO:1:

TTCAACGTGA CCTTCCGGAG GGCCAAGGGC TACCCCATCG ACCTGTACTA CCTGATGGAC    60

CTCTCCTACT CCATGGTGGA T    81

( 2 ) INFORMATION FOR SEQ ID NO:2:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bos taurus ( i x ) FEATURE:
        ( A ) NAME/KEY: mutation
        ( B ) LOCATION: replace(43, "t")

( x i ) SEQUENCE DESCRIPTION: SEQ ID NO:2:

GCGTGCCCGG AGGAAATCGG CTGGCGCAAT GTCACCAGGC TGCTGGTGTT CGCCACGGAC    60

GATGGGTTCC ACTTTGCGGG CGAT    84

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bos taurus ( x i ) SEQUENCE DESCRIPTION: SEQ ID NO:3:

TCCGGAGGGC CAAGGGCTA    19

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bos taurus ( x i ) SEQUENCE DESCRIPTION: SEQ ID NO:4:

GAGTAGGAGA GGTCCATCAG GTAGTACAGG 30

DIAGNOSTIC ASSAYS FOR GENETIC MUTATIONS ASSOCIATED WITH BOVINE LEUKOCYTE ADHESION DEFICIENCY

BACKGROUND OF THE INVENTION

1. Field of Invention

Leukocyte adhesion deficiency (LAD), formerly known as bovine granulocytopathy syndrome, was identified in cattle, and was found to cause unthriftiness and death at an early age [Hagemoser, W. A. et al., "Granulocytopathy in a Holstein heifer." J. Am. Vet. Med. Assoc., vol. 183, pp. 1093–1094 (1983); Nagahata, H. et al., "Bovine granulocytopathy syndrome: Neutrophil dysfunction in Holstein Friesian calves." J. Vet. Med. A, vol. 34, pp. 445–451 (1987); Takahashi, K. et al., "Bovine granuloctypathy syndrome of Holstein-Friesian calves and heifers." Jpn. J. Vet. Sci., vol. 49, pp. 733–736 (1987)]. Recently, this disease was shown to be equivalent to human LAD disease [Kehrli, M. E., Jr. et al., "Molecular definition of the bovine granulocytopathy syndrome: Identification of deficiency of the Mac-1 (CD11b/CD18) glycoprotein." Am. J. Vet. Res., vol. 51, pp. 1826–1836 (1990)]. In humans, LAD is an autosomal recessive genetic disease which results from various distinct mutations in the gene for the leukocyte adhesion molecule, CD18 [Anderson, D. C. et al., "The severe and moderate phenotypes of heritable Mac-1, LFA-1 deficiency: Their quantitative definition and relation to leukocyte dysfunction and clinical features." J. Infect. Dis., vol. 152, pp. 668–689 (1985)]. Preliminary studies indicated that there is only one defective allele in cattle and that the carrier frequency for LAD is high among Holstein cattle.

There are approximately 1100 young bulls introduced per year into progeny milk production testing programs in the United States. To achieve this number of bulls, approximately 1500 bulls per year are evaluated by bull stud organizations as candidates for the young sire evaluation program. To eliminate bovine leukocyte adhesion deficiency (BLAD) from the Holstein population, it is essential to know the BLAD carrier status of these bulls and also of a significant number of cows. Up to 20% of the Holstein Friesian cattle in the world may be carriers of this undesirable trait.

This invention relates to identifying a point mutation in the CD18 gene responsible for causing bovine leukocyte adhesion deficiency (BLAD) and to procedures used for testing and identifying cattle alleles attributable to BLAD.

2. Description of the Prior Art

Prior to this invention, the only test for detecting carriers utilized flow cytometry. Although this technique works well for detecting cattle with BLAD, its ability to distinguish BLAD carriers from normal cattle is limited because such testing is cumbersome and results are often ambiguous.

Recent developments in molecular biology have made it possible to rapidly and conclusively screen individuals for particular genetic defects. To make use of this technology, the genetic defect must be defined at the DNA level. Once this has been accomplished, various techniques can be employed to screen animals for the characteristic DNA sequence and thus their genetic status, i.e., homozygous normal, heterozygous carrier, or homozygous diseased, will be known.

Bovine citrullinemia, another bovine autosomal recessive disease, was recently defined at the DNA level [Dennis, J. A. et al., "Molecular definition of bovine argininosuccinate synthetase deficiency." Proc. Natl. Acad. Sci. U.S.A., vol. 86, pp. 7947–7951 (1989)]. A point mutation in the gene for bovine argininosuccinate synthetase was found to be the basis for this disease. By knowing the site of this mutation and adjacent DNA sequence information, a diagnostic test was developed. This test utilized DNA amplification followed by restriction enzyme digestion, and made identification of normal, carrier, and citrullinemic cattle possible. Citrullinemia is a separate genetic defect that is not linked to BLAD.

SUMMARY OF THE INVENTION

We have now determined both the cDNA sequence for CD18 in a normal (neither afflicted with nor a carrier of BLAD) cow and also the cDNA sequence for CD18 in a calf afflicted with BLAD. Upon comparing the two sequences, two differences were identified. The first difference was at nucleotide position 383 where the normal allele contained an adenine while the BLAD allele contained a guanine. The second difference occurred at nucleotide position 775 where the normal allele contained a cytosine while the BLAD allele contained a thymine. Either of these mutations can be used in any of a variety of assays to determine the genetic status of a cow for BLAD.

In accordance with this discovery, it is an object of the invention to provide the means for rapid and effective alternatives to flow cytometry for detecting BLAD in cattle.

Another object of the invention is to provide the means for facile diagnostic assays which are able to distinguish BLAD carriers from normal cattle.

It is a specific object of the invention to identify the DNA sequences encompassing nucleotide positions 383 and 775 and to apply this sequence information to design nucleic acid probes and primers for use in diagnostic assays for the defective allele.

An ultimate object of the invention is to cull BLAD carrier cattle from breeding stock and thereby eradicate BLAD from commercial cattle herds.

Other objects and advantages of this invention will become readily apparent from the ensuing description.

GLOSSARY

For purposes of this invention, the following standard abbreviations and terms used herein have been defined below. Also included are a listing of biological materials and reagents mentioned in the specification.

ABBREVIATIONS

ASO = allele specific oligomer
bp = base pairs
BLAD = bovine leukocyte adhesion deficiency
cDNA = single-stranded DNA complementary to a messenger RNA
DNA = deoxyribonucleic acid
LAD = leukocyte adhesion deficiency
RFLP = restriction fragment length polymorphism
RNA = ribonucleic acid.

TERMS

DNA or RNA sequence: a linear series of nucleotides connected one to the other by phosphodiester bonds between the 3' and 5' carbons of adjacent pentoses.

hybridization: the pairing together or annealing of complementary single-stranded regions of nucleic acids to form double-stranded molecules.

oligonucleotide: a linear series of 2-100 deoxyribonucleotides or ribonucleotides connected one to the other by phosphodiester bonds between the 3' and 5' carbons of adjacent pentoses.

nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), quanine ("G"), cytosine ("C") and thymine ("T"). The four RNA bases are A, G, C and uracil ("U").

oligonucleotide probe: a single-stranded piece of DNA or RNA that can be used to detect, by hybridization or complementary base-pairing, a target nucleic acid sequence which is homologous or complementary.

probe: a nucleic acid sequence (DNA or RNA) that can be used to detect, by hybridization or complementary base-pairing, another nucleic acid sequence which is homologous or complementary.

restriction site: A nucleotide sequence, usually 4 to 6 base pairs long, which is recognized and susceptible to cleavage in a specific fashion by a restriction enzyme.

sequence: two or more DNA or RNA nucleotides in a given order.

stringency: refers to the conditions under which hybridization takes place. At high stringency only exact matches of DNA and RNA will hybridize stably. Under low stringency, 80-90% homologous sequences may still hybridize.

| Restriction Enzyme | Cleavage Site |
|---|---|
| HaeIII | 5'...GG  CC...3' |
| TaqI | 5'...T  CGA...3' |

DETAILED DESCRIPTION OF THE INVENTION

The essence of the invention was the discovery and identification of a point mutation in the gene for bovine CD18 as well as the subsequent determination that this point mutation is responsible for BLAD. The mutation occurs at nucleotide 383 of the CD18 gene. A region of the normal gene containing the nucleotide 383 is given as SEQ ID NO 1, wherein nucleotide 383 is represented as base 41. A second mutation occurring at nucleotide 775 was identified in the CD18 gene, but does not cause disease. However, this latter mutation is closely linked to the etiologic mutation at nucleotide 383 and is therefore useful as a genetic marker for the disease. A region of the normal CD18 gene containing the nucleotide 775 is given as SEQ ID NO 2, wherein nucleotide 775 is represented as base 43.

Using the aforementioned sequence data, a variety of diagnostic assays could be applied to a DNA or RNA sample from a test animal for the purpose of determining the genetic status of the animal in regard to BLAD. Using the sequence data given in SEQ ID NO 1 and SEQ ID NO 2, primers can be constructed for amplifying a region encompassing base 383 or base 775. The amplified DNA can then be assayed by any of a variety of methods to ascertain the genotype. Alternatively, nucleic acid probes could be readily designed by the person in the art for use in a hybridization assay of the DNA or RNA from the test animal.

A rapid screening test based on RFLP was developed to determine the nucleotide at position 383, and thus the genetic status of a cow with respect to BLAD. In accordance with this test, a crude preparation of DNA is first prepared from tissues of a cow of interest. The DNA is amplified using oligonucleotide primers which bracket nucleotide 383. The amplified product is then subjected to restriction enzyme digestion with TaqI or HaeIII. TaqI specifically cuts the normal allele, while HaeIII cuts the BLAD allele. Digestion products are then determined by ethidium bromide stained gel electrophoresis. Further details of this assay are given below in Example 2.

Another embodiment of the invention utilizes bovine CD18 allele-specific oligomers (ASOs) to identify which alleles a particular cow, bull, calf, or embryo is carrying. Sample preparation for the ASO assay is similar to that for the RFLP technique described above. The difference in the methods is that, instead of a restriction endonuclease digestion to characterize the genotype, the amplified DNA is usually bound onto two solid supports (e.g., a nylon or nitrocellulose membrane) by standard techniques and then each membrane is placed into separate hybridization reactions. Hybridization reactions utilize two oligonucleotides that are synthesized so that one oligonucleotide is complementary to the normal DNA sequence and the other oligonucleotide is complementary to the mutated DNA sequence. The oligonucleotides are designed so that the mutation point hybridizes approximately in the middle of the probe sequence. The ASOs can be 10 to 30 bases, and preferably about 15 to 25 base pairs in length. The ASOs are labelled with radioactive material or a color or light producing reagent that allows for detection of allele specific hybridization of the ASO.

Stringent conditions in each hybridization reaction are set for preferential binding of one oligonucleotide probe to only the allele it is exactly complementary to. The other hybridization reaction is optimal for the other allele to be bound. Each hybridization reaction contains one of the oligonucleotide probes that is labeled with a marker (e.g., radioisotopic, colorimetric, or a chemiluminescent emitting) material that is detected after washing away the nonbound probes. These detection systems can then be visualized by various standard techniques and the results from the two hybridization reaction chambers are compared. If an oligonucleotide probe was found to bind to the test DNA on only one membrane, then the bovine source of the DNA is homozygous for the particular allele which that hybridization reaction was designed to bind. If the oligonucleotide probes are found to hybridize the test DNA on both membranes then the bovine source of the DNA is a heterozygous carrier. An example of this technique applied to detection of cystic fibrosis heterozygotes is Lemna, W. K. et al., "Mutation analysis for heterozygote detection and the prenatal diagnosis of cystic fibrosis." N. Eng. J. Med., vol. 322, pp. 291-296 (1990).

The following examples are intended only to further illustrate the invention and are not intended to limit the scope of the invention which is defined by the claims.

EXAMPLE 1

Determination of the point mutation for BLAD

The normal cDNA sequence for the bovine CD18 gene was determined in an cow suspected to be homozygous-normal on the basis of flow cytometric staining of leukocytes with a monoclonal antibody that binds the normal bovine CD18 gene product on the surface of leukocytes. A calf afflicted with BLAD was then found and purchased. The cDNA sequence of the CD18 gene in this calf afflicted with BLAD was determined and compared to the sequence for CD18 in the normal bovine. Two DNA sequence differences in the alleles for bovine CD18 were identified between the two sequences. The first difference was at nucleotide position 383 where the normal allele contained an adenine while the BLAD allele contained a guanine. The second difference occurred at nucleotide position 775 where the normal allele contained a cytosine while the BLAD allele contained a thymine. The mutation at position 383 caused a change in the deduced amino acid sequence for CD18. In the BLAD allele, an aspartic acid was replaced by a glycine in a highly conserved region of the CD18 protein. The mutation at position 775 was a silent mutation as it did not alter the deduced amino acid sequence.

To verify that these point mutations identify the BLAD allele, five calves which were known to be afflicted with clinical symptoms consistent with BLAD were screened for the presence of guanine at nucleotide position 383. All BLAD calves were found to contain only guanine at this position in their CD18 alleles. Several parents of these BLAD calves (obligate heterozygotes) were screened for the presence of adenine or guanine at nucleotide position 383; all were found to contain both adenine and guanine. In addition several homozygous-normal animals were found to contain only adenine at this position. The tested animals were of varying degrees of genetic relatedness (some closely related to each other, some more distantly related).

EXAMPLE 2

RFLP assay

A method was developed to rapidly screen animals for the mutation at position 383 so that their genetic status with respect to BLAD could be conclusively determined. The method involves DNA amplification using oligonucleotide primer which are specific to regions adjacent to nucleotide position 383. The sense primer sequence was 5'-TCCGGAGGGCCAAGGG-CTA-3' which corresponds to nucleotides 356-374 of the bovine CD18 cDNA sequence (SEQ ID NO 3). The antisense primer sequence was 5'-GAGTAG-GAGAGGTCCATCAGGTAGTACAGG-3' which corresponds to nucleotides 384-413 (SEQ ID NO 4). These oligonucleotide primers were commercially prepared by standard oligonucleotide synthesis techniques (I.S.U. Nucleic Acid Facility, Ames, Iowa). Other reagents for the amplification were purchased and used as described by the manufacturer (Prekin-Elmer Cetus, Norwalk, Conn.). A two-step amplification strategy was employed with temperature parameters of 94° C. for 15 sec and 69° C. for 20 sec for 30-35 cycles. The amplified DNA product was then split and separately subjected to restriction endonuclease digestion with TaqI and HaeIII. These enzymes were from commercial sources, and were added directly to the amplification products. Digestion reactions were incubated for at least 1 hr at 65° C. for TaqI and 37° C. for HaeIII. If the nucleotide at position 383 in the amplified DNA was an adenine, TaqI cut the 58 bp amplified product to generate 26 and 32 bp fragments. HaeIII cut the amplified products to generate 3, 6, and 49 bp fragments if the nucleotide at position 383 was an adenine. HaeIII cut the amplified product one more time if the nucleotide at position 383 was a guanine; the resulting fragment sizes were 3, 6, 19, and 30 bp. Fragment sizes after enzyme digestion were determined by 4% agarose gel electrophoresis and ethidium bromide staining. Complete cutting by TaqI indicated that the DNA was from a normal animal. Complete cutting by HaeIII at both positions indicated that the DNA was from a homozygous BLAD animal. Partial cutting by TaqI and HaeIII indicated that the DNA was from a carrier animal. Complete cutting by the restriction endonuclease digestion is evident when the 58-mer amplification product does not appear as a band on the gel. Partial cutting is evident when the 58-mer amplification product does appear as a band on the gel along with the expected fragments described above for each restriction endonuclease.

It is understood that the foregoing detailed description is given merely by way of illustration and that modification and variations may be made therein without departing from the spirit and scope of the invention.

---

We claim:

1. A method for distinguishing a normal CD18 protein allele from a defective CD18 protein allele in a bovine animal comprising assaying the nucleic acid of said animal for a point mutation at either base 383 or base 775 in the gene encoding said protein.

2. A method as described in claim 1 wherein the assay is allele specific oligomer hybridization.

3. A method as described in claim 1 comprising amplifying a region of nucleic acid comprising either base 383 or base 775, subjecting the amplified region to restriction endonuclease digestion with at least one enzyme which will discriminate between the normal allele and the defective allelle, and assaying the digestion products to determine the absence or presence of said point mutation.

4. A method as described in claim 3 comprising conducting the amplification of the region comprising base 383 by polymerase chain reaction using a set of primers, wherein one of the primers of the set consists of a sequence from SEQ ID NO 3 and the other one of the primers of the set consists of a sequence from SEQ ID NO 4.

5. A method as described in claim 1 comprising amplifying a region of nucleic acid comprising either base 383 or base 775, subjecting the amplified region to stringent hybridization conditions with a oligonucleotide probe which is preselected to be complementary to either the normal allele or the defective allele, and assaying for hybridization.

6. A method as described in claim 5, wherein said probe is about 12 to about 25 bases in length.

7. A method as described in claim 6, wherein said probe consists of a sequence, or the complement of a sequence, from a region of SEQ ID NO 1 including base 41 thereof corresponding to base 383 of the gene.

8. A method as described in claim 6, wherein said probe consists of a sequence, or the complement of a sequence, from a region of SEQ ID NO 2 including base 43 thereof corresponding to base 775 of the gene.

9. A single-stranded oligonucleotide probe having a length limited to about 12 to 30 bases and selected from the group consisting of:

(1) a nucleic acid sequence consisting of a sequence, or the complement of a sequence, from a region of SEQ ID NO 1 including base 41, which base corresponds to base 383 of the gene; and (2) a nucleic acid sequence consisting of a sequence, or the complement of a sequence, from a region of SEQ ID NO 2 including base 43, which base corresponds to base 775 of the gene.

10. A single-stranded oligonucleotide primer consisting of a sequence limited to about 12 to 30 contiguous bases from SEQ ID NO 1 or its complement, wherein said sequence is either 5' or 3' from base 41 of SEQ ID NO 1.

11. A primer as described in claim 10 and consisting of the 19-base sequence of SEQ ID NO 3.

12. A primer as described in claim 10 and consisting of the 30-base sequence of SEQ ID NO 4.

13. A method as described in claim 1 wherein the assay is restriction endonuclease digestion with a restriction endonuclease which recognizes either the normal sequence which encompasses base 383 or a defective sequence which encompasses base 383, but not both.

14. A method as described in claim 1 wherein the assay is restriction endonuclease digestion with a restriction endonuclease which recognizes either the normal sequence which encompasses base 775 or a defective sequence which encompasses base 775, but not both.

* * * * *